United States Patent
Ohashi et al.

(10) Patent No.: US 10,174,208 B2
(45) Date of Patent: Jan. 8, 2019

(54) CURABLE RESIN COMPOSITION HAVING ANTIBACTERIAL POWER

(71) Applicant: TOYO SEIKAN GROUP HOLDINGS, LTD., Tokyo (JP)

(72) Inventors: Kazuaki Ohashi, Yokohama (JP); Yasuhiro Kosaka, Yokohama (JP); Akiko Ogata, Yokohama (JP); Hiroshi Shimomura, Osaka (JP); Akira Ishiko, Osaka (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 0 days.

(21) Appl. No.: 15/037,578

(22) PCT Filed: Nov. 21, 2014

(86) PCT No.: PCT/JP2014/080954
§ 371 (c)(1),
(2) Date: May 18, 2016

(87) PCT Pub. No.: WO2015/076385
PCT Pub. Date: May 28, 2015

(65) Prior Publication Data
US 2016/0289459 A1 Oct. 6, 2016

(30) Foreign Application Priority Data

Nov. 22, 2013 (JP) .................. 2013-242377

(51) Int. Cl.
| | | |
|---|---|---|
| *C09D 5/14* | (2006.01) |
| *C08K 9/04* | (2006.01) |
| *B22F 1/00* | (2006.01) |
| *C09D 133/00* | (2006.01) |
| *A01N 59/16* | (2006.01) |
| *C08K 3/08* | (2006.01) |

(52) U.S. Cl.
CPC .............. *C09D 5/14* (2013.01); *A01N 59/16* (2013.01); *B22F 1/0018* (2013.01); *B22F 1/0062* (2013.01); *C08K 9/04* (2013.01); *C09D 133/00* (2013.01); *B22F 2001/0092* (2013.01); *C08K 2003/0806* (2013.01); *C08K 2201/005* (2013.01); *C08K 2201/011* (2013.01)

(58) Field of Classification Search
CPC .............. C08K 9/04; C08K 2201/005; C08K 2201/011; C08K 2003/0806; C09D 5/14; C09D 133/00; B22F 1/0018; B22F 2001/0092; B22F 1/0062
See application file for complete search history.

(56) References Cited

U.S. PATENT DOCUMENTS

| | | |
|---|---|---|
| 6,358,611 B1 | 3/2002 | Nagasawa et al. |
| 6,743,395 B2 | 6/2004 | Fukunaga et al. |
| 6,871,773 B2 | 3/2005 | Fukunaga et al. |
| 8,106,228 B2 | 1/2012 | Ohashi et al. |
| 2011/0002872 A1 | 1/2011 | Ohashi et al. |
| 2013/0126798 A1 | 5/2013 | Nakatani |
| 2013/0153835 A1 | 6/2013 | Hinotsu et al. |
| 2013/0265735 A1 | 10/2013 | Nakatani et al. |

FOREIGN PATENT DOCUMENTS

| | | |
|---|---|---|
| EP | 3 064 296 A1 | 9/2016 |
| JP | 8-311373 A | 11/1996 |
| JP | 10-183207 A | 7/1998 |
| JP | 3205793 B2 | 9/2001 |
| JP | 2004-143374 A | 5/2004 |
| JP | 2009-74171 A | 4/2009 |
| JP | 2009-209052 A | 9/2009 |
| JP | 2009-209387 A | 9/2009 |
| JP | 2009-226400 A | 10/2009 |
| JP | 4448551 B2 | 4/2010 |
| JP | 2011-57855 A | 3/2011 |
| JP | 2011-238596 A | 11/2011 |
| JP | 2012-2978 A | 1/2012 |
| JP | 2012-23014 A | 2/2012 |
| JP | 2012-117099 A | 6/2012 |
| JP | 2012-207049 A | 10/2012 |
| JP | 2013-241643 A | 12/2013 |
| WO | 01/70435 A1 | 9/2001 |
| WO | 2008/062548 A1 | 5/2008 |
| WO | 2011/007650 A1 | 1/2011 |
| WO | 2011/152406 A1 | 12/2011 |
| WO | 2012/059974 A1 | 5/2012 |

OTHER PUBLICATIONS

International Search Report of PCT/JP2014/080954 dated Feb. 3, 2015.
Communication dated Jun. 22, 2017 from the European Patent Office in counterpart Application No. 14864464.4.
Communication dated Jun. 12, 2018, from the Japanese Patent Office in counterpart application No. 2014-236848.

*Primary Examiner* — Sanza L. McClendon
(74) *Attorney, Agent, or Firm* — Sughrue Mion, PLLC

(57) ABSTRACT

A curable resin composition including a curable resin in which ultrafine metal particles modified with a fatty acid are dispersed. The ultrafine metal particles are fatty acid-modified ultrafine metal particles having a fatty acid coordinated on the surfaces of the ultrafine metal particles and a glyceride coordinated around the fatty acid or on the surfaces of the ultrafine metal particles.

6 Claims, No Drawings

CURABLE RESIN COMPOSITION HAVING ANTIBACTERIAL POWER

CROSS REFERENCE TO RELATED APPLICATIONS

This application is a National Stage of International Application No. PCT/JP2014/080954 filed Nov. 21, 2014, claiming priority based on Japanese Patent Application No. 2013-242377, filed Nov. 22, 2013, the contents of all of which are incorporated herein by reference in their entirety.

TECHNICAL FIELD

This invention relates to an antibacterial resin composition containing ultrafine metal particles. More specifically, the invention relates to a curable resin composition in which ultrafine metal particles are favorably dispersed, exhibiting excellent optical properties and being very suited from the standpoint of productivity.

BACKGROUND ART

Ultrafine metal particles of the order of nanometers exhibit properties different from those of general materials, such as large specific surface areas and specific properties depending on their quantum size effect. Therefore, their study and use have been forwarded in a variety of fields such as of electronic materials, magnetic materials, optical materials, osmotic films, catalytic materials, antibacterial agents and the like.

The ultrafine metal particles, on the other hand, are highly active, unstable, cannot maintain the state of ultrafine particles their form of a simple substance and, therefore, tend to aggregate together. In the use where optical properties are required, therefore, the ultrafine metal particles are accompanied by such problems as low transparency, poor properties or without at all exhibiting properties.

In the step of preparing ultrafine metal particles, further, the handling property decreases causing, therefore, a decrease in the productivity. Thus the ultrafine metal particles had not still been fully satisfactory because of their poor transparency and poor productivity. To solve these problems, therefore, some proposals have been made as described below.

For instance, a patent document 1 listed below is proposing ultrafine metal composite particles forming a shell of an organometal compound surrounding the metal. The present applicant has earlier proposed a resin composition containing ultrafine metal particles formed by blending a resin with a fatty acid metal salt followed by heating (patent document 2). There has, further, been proposed a method of producing ultrafine metal particles by mixing a metal salt and a chemically adsorptive organic compound containing a functional group together, and heating and reacting them together (patent document 3).

There are many prior arts related to the use of optical materials, such as acrylic resin containing a quaternary ammonium compound as an antibacterial agent (patent document 4), a photocurable composition for antibacterial coating comprising a photocurable acrylic resin that contains a silver salt (patent document 5), and a resinous formed body such as boards having antibacterial power for protecting various display devices, comprising a photocurable resin and an antibacterial agent and/or an anti-molding agent contained therein (patent document 6).

PRIOR ART DOCUMENTS

Patent Documents

Patent document 1: Japanese Patent No. 3205793
Patent document 2: Japanese Patent No. 4448551
Patent document 3: WO01/70435
Patent document 4: JP-A-2011-57855
Patent document 5: JP-A-8-311373
Patent document 6: WO2011/007650

OUTLINE OF THE INVENTION

Problems that the Invention is to Solve

According to the above patent document 1, however, the ultrafine metal particles are coated with an organometal compound, and are not still fully satisfactory in regard to dispersion property and productivity.

The resin composition containing ultrafine metal particles described in the patent document 2 is the one obtained by blending a resin with a fatty acid metal salt followed by heating. The resin composition is capable of imparting antibacterial power to the resinous formed bodies and is advantageous in regard to productivity and preventing the ultrafine metal particles from aggregating. The resin composition, however, permits the ultrafine metal particles to vary their properties depending on the heating, kneading and time, and is not still fully satisfactory from the standpoint of controlling the production.

Further, a patent document 3 describes a method of producing ultrafine metal particles and a patent document 4 describes blending an acrylic acid with an antibacterial agent. However, the ultrafine metal particles in the form of a simple substance have such a high activity that they undergo aggregation if they are added to the acrylic resin and may disperse poorly.

Patent documents 5 and 6 are describing resin compositions obtained by blending a photocurable acrylic resin with a silver salt, in which, however, the silver salt cannot be efficiently and homogeneously dispersed in the resin and, therefore, silver ions cannot be effectively eluted out. Namely, it is not possible to obtain a resin composition satisfying both the requirement of antibacterial power and the requirement of economy. Besides, the silver salt that undergoes the aggregation may cause excellent transparency of the resin to decrease.

It is, therefore, an object of the present invention to provide a curable resin composition that features excellent dispersion property and productivity, enables metals such as silver and the like having antibacterial power to be efficiently eluted out, and is capable of expressing excellent antibacterial power.

Another object of the present invention is to provide an antibacterial curable resin composition capable of expressing antibacterial power despite it contains ultrafine metal particles modified with a fatty acid having excellent dispersion property even in small amounts.

Means for Solving the Problems

According to the present invention, there is provided a curable resin composition including a curable resin and ultrafine metal particles dispersed in the curable resin, wherein the ultrafine metal particles are modified with a fatty acid.

In the curable resin composition of the present invention, it is desired that:

(1) an ion stabilizer is, further, contained;
(2) said fatty acid is coordinated on surfaces of the ultrafine metal particles, and a glyceride coordinated round said fatty acid or on the surfaces of the ultrafine metal particles;
(3) the curable resin is a photocurable resin;
(4) the ultrafine metal particles are the ultrafine silver particles;
(5) the curable resin composition contains a dispersion solution that contains the ultrafine metal particles modified with the fatty acid; and
the dispersion solution that contains the ultrafine metal particles modified with the fatty acid is a low-boiling solvent that contains the ultrafine metal particles modified with the fatty acid, that is obtained by using a glycerin as a high-boiling solvent, adding a fatty acid metal salt of a metal of any one of Ag, Cu or Zn and a saccharin to the high-boiling solvent, heating and mixing them together to thereby prepare the high-boiling solvent in which the ultrafine metal particles modified with the fatty acid are dispersed, the ultrafine metal particles modified with the fatty acid being the ultrafine metal particles of any one of Ag, Cu or Zn and having the fatty acid and the glyceride coordinated on the surfaces thereof, mixing the high-boiling solvent in which the ultrafine metal particles modified with the fatty acid are dispersed and a low-boiling solvent together and, thereafter, isolating the high-boiling solvent and the low-boiling solvent into two phases so that the ultrafine metal particles modified with the fatty acid are extracted from the high-boiling solvent into the low-boiling solvent;
(6) the low-boiling solvent is methylisobutyl ketone or methyl ethyl ketone; and
(7) a difference is not more than 3 between a solubility parameter (SP value) of the fatty acid or the glyceride and a solubility parameter (SP value) of the low-boiling solvent.

Effects of the Invention

The curable resin composition of the present invention has excellent antibacterial power and transparency since the ultrafine metal particles modified with the fatty acid are favorably dispersed therein without being aggregated. Here, the word antibacterial stands for suppressing the propagation or proliferation of bacteria.

The solvent for diluting the curable resin contains a fatty acid-modified ultrafine metal particle-containing dispersion solution that comprises a low-boiling solvent containing fatty acid-modified ultrafine metal particles having a glyceride coordinated round the fatty acid or on the surfaces of the particles. Therefore, it is allowed to prepare a curable resin composition containing fatty acid-modified ultrafine metal particles capable of exhibiting the above-mentioned effects maintaining very favorable productivity.

According to the present invention, further, the solvent for diluting the curable resin contains the ultrafine metal particles modified with the fatty acid. Therefore, the fatty acid-modified ultrafine metal particles that are formed can be dispersed in the resin without the need of taking them out from the solvent, offering advantage from the standpoint of production.

Moreover, the glyceride is coordinated round the fatty acid that is coordinated on the surfaces of the ultrafine metal particles, or is coordinated on the surfaces of the particles. The glyceride is very favorably compatible with the low-boiling solvent. As will be described later, therefore, this accelerates the extrusion of the glyceride from the high-boiling solvent into the low-boiling solvent. It is, therefore, made possible to prepare a fatty acid-modified ultrafine metal particle-containing dispersion solution that comprises the low-boiling solvent that contains the fatty acid-modified ultrafine metal particles dispersed therein at a high concentration and maintaining good stability.

As described above, the curable resin composition of the invention can be added to a coating material or can be applied maintaining the state of the fatty acid-modified ultrafine metal particles having an average primary particle diameter of not more than 100 nm, and features excellent transparency and antibacterial power. These effects will become obvious even from the results of Examples appearing later.

That is, in the case of a resin composition containing the dispersion solution that contains the fatty acid-modified ultrafine silver particle, the glyceride monostearate is added into the dispersion solution that contains the fatty acid-modified ultrafine silver particles so as to be coordinated on the surfaces of the ultrafine silver particles enabling the ultrafine silver particles to be dispersed in the resin composition without being aggregated. As a result, the resin composition does not lose its transparency and exhibits high antibacterial power maintaining excellent transparency (Examples 1 to 3).

On the other hand, if there is used no dispersion solution containing fatty acid-modified ultrafine silver particles, then no antibacterial effect is exhibited (Comparative Example 1). If there is used a dispersion solution containing a silver ion-exchange zeolite which is a conventional silver type antibacterial agent, the antibacterial effect is not exhibited if the amount thereof is small. If the amount thereof is large, on the other hand, transparency is impaired since the particles have large diameters causing the legibility to decrease. Therefore, the resin composition cannot be used for the optical products (Comparative Examples 2 and 3).

By using the silver stearate, a powder of fatty acid-modified ultrafine silver particles was prepared in compliance with the Japanese Patent No. 3205793 and was mixed into the methylisobutyl ketone to obtain a dispersion solution containing fatty acid-modified ultrafine silver particles. In this case, the dispersion property in the solution was inferior to those of Examples 1 to 3. Namely, the particles dispersed poorly in the acrylic resin, and no antibacterial effect was exhibited (Comparative Example 4). By using the silver stearate, fatty acid-modified ultrafine silver particles were prepared in compliance with the Japanese Patent No. 3205793 and were mixed directly into the UV acrylic resin. In this case, the dispersion property was worse, and brown aggregates of silver particles were recognized on the coating (Comparative Example 5).

MODES FOR CARRYING OUT THE INVENTION (Ultrafine Metal Particles Modified with the Fatty Acid)

As the fatty acid used for forming the fatty acid-modified ultrafine metal particles of the invention, there can be exemplified aliphatic carboxylic acids such as myristic acid, stearic acid, oleic acid, palmitic acid, n-decanoic acid, paratoluic acid, succinic acid, malonic acid, tartaric acid, malic acid, glutaric acid, adipic acid and acetic acid; aromatic carboxylic acids such as phthalic acid, maleic acid, isophthalic acid, terephthalic acid, benzoic acid and naphthenic acid; and alicyclic carboxylic acids such as cyclohexanedicarboxylic acid and the like.

In the present invention, the fatty acid that is used is, desirably, a higher fatty acid such as myristic acid, stearic acid or palmitic acid and, particularly desirably, the one having a branch and a large number of carbon atoms.

As the fatty acid metal salt which is a preferred starting material of the fatty acid-modified ultrafine metal particles, there can be exemplified, particularly, a silver myristate and a silver stearate. It is, further, desired that the fatty acid-modified ultrafine metal particles are comprised of a metal at the centers thereof and have an average particle diameter in a range of 1 to 500 μm and, specifically, 10 to 200 μm. The average particle diameter referred to in the specification is an average value of the particles each of which having no gap between metal and metal.

The metal component of the ultrafine metal particles is at least one kind of those selected from the group consisting of Cu, Ag, Au, Id, Pd, Pt, Fe, Ni, Co, Zn, Nb, Ru and Rh. From the standpoint of antibacterial power, however, silver, copper and zinc are preferred, and silver is particularly preferred.

(Curable Resins)

As the curable resin used for the curable resin composition of the invention, there can be exemplified a photocurable resin, a thermosetting resin and a two-package type resin comprising amain agent and a curing agent that have heretofore been known. The photocurable resin, however, is desirably used. Described below are the photocurable resins.

[Photocurable Resins]

As the photocurable resin used for the resin composition of the invention, there can be used any known acrylic resins that can be cured upon being irradiated with light such as ultraviolet rays.

As the acrylic resin, there can be exemplified those comprising a monofunctional or bifunctional monomer having one or more (meth)acryloyl groups in a molecule thereof, a polyfunctional monomer, a polyfunctional oligomer or a polyfunctional polymer.

As the monofunctional or bifunctional monomer, polyfunctional monomer, polyfunctional oligomer or polyfunctional polymer, there can be exemplified polyester (meth)acrylate, polyurethane (meth)acrylate, epoxy (meth)acrylate, trimethylolpropane tri(meth)acrylate, ditrimethylolpropane tetra(meth)acrylate, glycerol tri(meth)acrylate, tris((meth)acryloyloxyethyl) isocyanulate, tris((meth)acryloyloxypropyl) isocyanulate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, dipentaerythritol hexa(meth)acrylate, tripentaerythritol tetra(meth)acrylate tripentaerythritol penta(meth)acrylate, tripentaerythritol hexa(meth)acrylate, tripentaerythritol hepta(meth)acrylate, tripentaerythritol octa(meth); cyclohexyl (meth)acrylate, lauryl (meth)acrylate, stearyl (meth)acrylate, benzyl (meth)acrylate, dicyclopentenyl (meth)acrylate, dicyclopentenyloxyethyl (meth)acrylate, tricyclodecanyl (meth)acrylate, isobonyl (meth)acrylate, isoamyl (meth)acrylate, t-butyl (meth)acrylate, methoxyethyl (meth)acrylate, ethoxyethyl (meth)acrylate, methoxyethoxyethyl (meth)acrylate, ethoxyethoxyethyl (meth)acrylate, phenoxyethyl (meth)acrylate, phenoxypropyl (meth)acrylate, tetrahydrofurfuryl (meth)acylate, 2-hydroxyethyl (meth)acrylate, 2-hydroxypropyl (meth)acrylate, (meth) acrylic acid, (meth)acryloylmorpholine, ethylene glycol di(meth)acrylate, 1,6-hexanediol di(meth)acrylate, 1,9-nonanediol di(meth)acrylate, diethylene glycol di(meth)acrylate, tripropylene glycol di(meth)acrylate, neopentyl glycol di(meth)acrylate, cyclohexane-1,4-dimethanol di(meth)acrylate, bisphenol A di(meth)acrylate, trimethyloethane di(meth)acrylate, tricyclodecanedimethanol di(meth)acrylate, trimethylolpropane di(meth)acrylate, ethylene oxide-modified bisphenol A di(meth)acrylate, neopentyl glycol-modified trimethylolpropane di(meth)acrylate, and bis-(2-(meth)acryloyloxyethyl) phthalate.

[Photopolymerization Initiators]

As the photopolymerization initiator, there can be used those that have heretofore been known. Concretely, there can be used 2,2-diethoxyacetophenone, benzyldimethylketal, benzophenone, methyl o-benzoylbenzoate, bis(4-dimethylaminophenyl) ketone, 1,2-diphenylethanedion, 2-phenyl-2-hydroxy-acetophenone, benzoinmethyl ether, benzoinethyl ether, benzoinisopropyl ether, benzoinisobutyl ether, 4'-isopropyl-2-hydroxy-2-methyl-propiophenone, 2-hydroxy-2-methyl-propiophenone, thioxanthone, 2-methylthioxanthone and 1-hydroxycyclohexylphenylketone.

It is also allowable to use a photosensitization assistant together with the photopolymerization initiator. As the photosensitization assistant, there can be used tertiary amines such as N,N-dimethyl-p-toluidine, tributylamine, N-methyldiethanolamine and p-dimethylaminobenzoic acid ethyl ester, as well as anthraquinone, 5-nitrofluorene and 5-nitroacenaphthene.

(Photocurable Resin Compositions)

The curable resin composition or the photocurable resin, according to the present invention, can be prepared by mixing a photocurable acrylic resin, a photopolymerization initiator, a diluent and a dispersion solution containing the fatty acid-modified ultrafine metal particles together. Here, as the diluent, it is desired to use the dispersion solution containing the fatty acid-modified ultrafine metal particles that will be described later. The dispersion solution, the photocurable resin and the photopolymerization initiator are, thereafter, mixed together.

As the diluent to be used in combination with the dispersion solution containing the ultrafine metal particles modified with the fatty acid, there can be used those that have heretofore been used as diluents for acrylic resins and, specifically, solvents having relatively small polarity and low boiling points, such as methyisobutyl ketone, methyl ethyl ketone, ethyl acetate and butyl acetate. This makes it possible to efficiently disperse the ultrafine metal particles modified with the fatty acid in the curable resin composition.

It is desired that the photocurable acrylic resin is blended with the dispersion solution which is diluted with the diluent into 5 to 100 times and, specifically, 10 to 50 times. This enables the photocurable acrylic resin composition to be blended with the antibacterial metal compound in a state of being homogeneously dispersed therein.

In the invention, the curable resin composition is blended with the dispersion solution that contains the ultrafine metal particles modified with the fatty acid prepared by a method that will be described later such that the amount of the ultrafine metal particles modified with the fatty acid is 0.005 to 0.5% by weight and, specifically, 0.01 to 0.2% by weight in the curable resin composition. If the amount of the ultrafine metal particles modified with the fatty acid is smaller than the above range, the antibacterial power may not often be obtained to a sufficient degree. If the amount of the antibacterial compound is larger than the above range, on the other hand, the antibacterial effect can be more enhanced accompanied, however, by disadvantage in economy and formability.

The photopolymerization initiator is used in an amount of, desirably, 0.5 to 3 parts by weight per 100 parts by weight of the photocurable acrylic resin.

The photocurable acrylic resin is, desirably, diluted with a solvent in advance and is, thereafter, mixed with the photopolymerization initiator, dispersion solution and diluent. As the solvent, there can be used any of those that have heretofore been used as solvents for the acrylic resins. Examples include methanol, ethanol, isopropanol, diethyl ether, methyl ethyl ketone, methylisobutyl ketone, ethyl acetate and butyl acetate though not limited thereto only. It is, however, desired to use the same diluent as the one mentioned above.

The photocurable resin composition of the present invention can be, further, blended with various known blending agents such as filler, plasticizer, leveling agent, viscosity-increasing agent, viscosity-decreasing agent, stabilizer, anti-oxidant, ultraviolet-ray absorber and the like within a range in which excellent properties possessed by the antibacterial resin composition of the invention, such as antibacterial power and transparency, are not impaired.

The photocurable acrylic resin composition of the present invention can be favorably used as a coating composition, coating agent or adhesive composition in a customary manner and can, further, be formed into resinous molded articles such as films, sheets, etc.

The curing conditions for forming films and resinous formed articles cannot be exclusively determined since they vary depending upon the kind of the acrylic resin that is used, upon the photopolymerization initiator or upon the kind of the diluent or the ultrafine metal particles modified with the fatty acid, or upon the viscosities thereof and upon the kind of the source of light. Usually, however, it is desired that the curable resin composition is irradiated with light in a range of 100 to 500 J/cm$^2$.

As the source of irradiating ultraviolet rays, though not limited thereto only, there can be used any known source of light such as chemical lamp, xenon lamp, low-pressure mercury lamp, high-pressure mercury lamp or metal halide lamp.

[Other Curable Resins]

As the thermosetting resin that can be used for the resin composition of the present invention, though not limited thereto only, there can be exemplified known thermosetting resins such as phenol resin, epoxy resin, urethane resin, melamine resin, urea resin, alkyd resin, unsaturated polyester resin and silicone resin. As the two-package type resin, there can be exemplified epoxy resin, silicone resin and the like resins.

[Ion Stabilizers]

The curable resin composition of the present invention, particularly preferably, contains an ion stabilizer from the standpoint of suppressing the metal ions from being reduced to an excess degree. This makes it possible to suppress the reduction of the ultrafine metal particles and to improve antibacterial power.

It is desired that the ion stabilizer dissolves partly or entirely in a low-boiling solvent or a high-boiling solvent, and has an acid dissociation constant (pka) of not more than 4.5. Examples thereof include salicylic acid (pKa 2.8), aspartic acid (pKa 1.93), citric acid (pKa 2.90), fumaric acid (pKa 2.9), benzoic acid (pKa 4.2), o-benzoic acid sulfimide (saccharin (pKa 2.2)), m-hydroxybenzoic acid (pKa 4.1), o-aminobenzoic acid (pKa 2.0), m-aminobenzoic acid (pKa 3.2), p-aminobenzoic acid (pKa 3.1), and a combination thereof. Here, pKa stands for an acid dissociation constant.

In the case of a polybasic acid, if a value of the first stage is denoted by Ka, then pKa is a value defined as −log Ka.

In the invention, as the fatty acid in the fatty acid metal salt used in combination with the ion stabilizer, there can be exemplified myristic acid, stearic acid, oleic acid, palmitic acid, n-decanoic acid, paratoluic acid, succinic acid, malonic acid, tartaric acid, malic acid, glutalic acid, adipic acid and acetic acid. Among them, the metal salt of stearic acid can be preferably used.

(Method of Producing a Dispersion Solution Containing the Ultrafine Metal Particles Modified with the Fatty Acid)

The fatty acid-modified ultrafine metal particle-containing dispersion solution contained in the curable resin composition of the invention can be prepared by the following two production methods.

(1) First Production Method.

(1-1) First Step.

In a first step in the first production method, fatty acid-modified ultrafine metal particles having a fatty acid or a glyceride coordinated on the surfaces thereof are formed in the glycerin that is the high-boiling solvent. There is no limitation on the conditions so far as the fatty acid-modified ultrafine metal particles can be formed. Preferably, however, the fatty acid metal salt of a metal of any of silver, copper or zinc and the saccharin are added to the glycerin. After the addition, the high-boiling solvent is heated at a temperature in a range of 120 to 230° C. and, specifically, 140 to 170° C. Though dependent upon the temperature of heating, the heating and mixing are continued for 10 to 120 minutes and, specifically, 30 to 80 minutes to thereby form the fatty acid-modified ultrafine metal particles in the glycerin, the fatty acid-modified ultrafine metal particles having the fatty acid and the glyceride coordinated on the surfaces thereof. That is, upon being heated in the above temperature range, the fatty acid metal salt is decomposed and reduced into the fatty acid and the metal that forms ultrafine metal particles, and the fatty acid is coordinated on the surfaces of the particles. The fatty acid and the glycerin undergo the esterification reaction to form the glyceride. Like the fatty acid, the glyceride, too, is coordinated on the surfaces of the ultrafine metal particles, and the fatty acid-modified ultrafine metal particles are dispersed in the glycerin.

Here, it is desired that the fatty acid metal salt which is the antibacterial component is contained in an amount of 0.1 to 2% by weight. If the amount of the fatty acid metal salt is less than the above range, the antibacterial power cannot be imparted to the dispersion solution to a sufficient degree. If the amount of the fatty acid metal salt is larger than the above range, on the other hand, the antibacterial effect can be reinforced bring about, however, disadvantage in economy and formability.

(1-2) Second Step.

Next, the low-boiling solvent is added to the glycerin that contains the fatty acid-modified ultrafine metal particles followed by stirring and mixing to prepare a mixed solution thereof. Here, as an assistant for extraction, other high-boiling solvents such as ethylene glycol and the like may also be added together with the low-boiling solvent.

The amount of the low-boiling solvent to be added cannot be exclusively determined but is, desirably, in a range of 10 to 200 parts by weight per 100 parts by weight of the high-boiling solvent that is used.

Other high-boiling solvents such as ethylene glycol and the like are added together with the low-boiling solvent, desirably, in amounts in a range of 50 to 100 parts by weight per 100 parts by weight of the low-boiling solvent.

(1-3) Third Step.

The mixed solution of the high-boiling solvent and the low-boiling solvent is left to standstill at a temperature of 0 to 40° C. for not less than 60 minutes to isolate the high-boiling solvent and the low-boiling solvent into phases and, thereafter, the high-boiling solvent is removed.

After the mixed solution is isolated into phases, the fatty acid-modified ultrafine metal particles having the fatty acid and the glyceride coordinated on the surfaces thereof are extracted from the high-boiling solvent into the low-boiling solvent. Here, the unreacted fatty acid metal salt and the aggregate that has turned into the metal itself due to over-reduction are left in the high-boiling solvent. By removing the high-boiling solvent, therefore, there is obtained a dispersion solution comprising the low-boiling solvent in which the fatty acid-modified ultrafine metal particles only are dispersed.

The high-boiling solvent can be removed by a customary method such as simple distillation, reduced pressure distillation, precision distillation, membrane distillation, extraction or membrane isolation.

(2) Second Production Method.

(2-1) First Step.

The principal object of the first step in the second production method is to form the ultrafine metal particles having the fatty acid coordinated thereon in the glycerin that is the high-boiling solvent. There is no limitation on the conditions so far as the fatty acid-modified ultrafine metal particles can be formed. Desirably, however, the fatty acid metal salt and the saccharin are added to the glycerin, and the high-boiling solvent thereof after the addition is heated at a temperature in a range of 120 to 230° C. and, specifically, 140 to 170° C. followed by mixing for 10 to 120 minutes and, specifically, 30 to 80 minutes.

In the second production method, too, like in the first production method, it is desired that the fatty acid-modified ultrafine metal particles are formed having the fatty acid and the glyceride coordinated on the surfaces thereof. This makes it possible to increase the content of the ultrafine metal particles in the final dispersion solution.

(2-2) Second Step.

Next, a mixed solution is prepared by adding a glyceride-containing low-boiling solvent to the glycerin that contains the fatty acid-modified ultrafine metal particles. Here, in the invention as described above, the other high-boiling solvents such as ethylene glycol and the like may be added thereto together with the low-boiling solvent.

By mixing the fatty acid-modified ultrafine metal particle-containing glycerin into the glyceride-containing low-boiling solvent, the fatty acid and the glyceride are coordinated on the surfaces of the ultrafine metal particles, and there are formed the same fatty acid-modified ultrafine metal particles as those formed by the first production method and at a high concentration.

The content of the glyceride in the low-boiling solvent varies depending on the content of the antibacterial component that is used, and cannot be exclusively determined but is, preferably, in a range of 0.02 to 5% by weight per 100 parts by weight of the low-boiling solvent.

Further, the amount of the glyceride-containing low-boiling solvent may vary depending on the content of the glyceride and the content of the antibacterial component, and cannot be exclusively specified but is, desirably, in a range of 10 to 200 parts by weight per 100 parts by weight of the high-boiling solvent.

It is, further, desired that the amount of the other high-boiling solvents such as ethylene glycol and the like added together with the low-boiling solvent, is in a range of 50 to 100 parts by weight per 100 parts by weight of the low-boiling solvent.

(2-3) Third Step.

Like in the first production method, the mixed solution of the high-boiling solvent and the low-boiling solvent is allowed to stand still at a temperature of 0 to 40° C. for not less than 60 minutes, whereby the high-boiling solvent and the low-boiling solvent are isolated into phases and, thereafter, the high-boiling solvent is removed.

(Dispersion Solution Containing the Fatty Acid-modified Ultrafine Metal Particles)

As described earlier, the fatty acid-modified ultrafine metal particle-containing dispersion solution that is contained in the curable resin composition of the present invention, comprises the low-boiling solvent such as methylisobutyl ketone or methyl ethyl ketone in which are dispersed fatty acid-modified ultrafine metal particles having an average primary particle size of not more than 100 nm and, specifically, 10 to 50 nm and having an average secondary particle size of not more than 900 nm and, specifically, 200 nm to 700 nm. If mixed to the curable resin composition, therefore, the dispersion solution containing the fatty acid-modified ultrafine metal particles does not cause a decrease in the transparency of the composition itself. The average primary particle size referred to in the specification stands for an average size of the metal particles that are present without gap among the metal particles. The average secondary particle size stands for an average size of the metal particles that are in a packed state.

Further, since the fatty acid-modified ultrafine metal particles are homogeneously dispersed without being conspicuously aggregated, excellent antibacterial power can be expressed.

In the dispersion solution containing the fatty acid-modified ultrafine metal particles, further, the ultrafine metal particles present in the dispersion solution have the fatty acid coordinated on the surfaces thereof and, further, have the glyceride coordinated around the fatty acid or on the surfaces thereof exhibiting, therefore, very excellent dispersion stability and without almost precipitating even after the passage of long periods of time. Therefore, the fatty acid-modified ultrafine metal particles disperse well and homogeneously even in the resin composition that constitutes a transparent material. In the dispersion solution, further, the fatty acid-modified ultrafine metal particles have the glyceride coordinated around the fatty acid or on the surfaces thereof. In the resin composition layer, therefore, the resin comes little into direct contact with the surfaces of the ultrafine metal particles. This effectively suppresses the decomposition of the resin, suppresses a decrease in the molecular weight of the resin, and effectively prevents the formability or the workability from being impaired.

(High-boiling Solvents)

A glycerin can be used as the high-boiling solvent for preparing the dispersion solution that contains the fatty acid-modified ultrafine metal particles. As the other high-boiling solvents used together with the glycerin, further, there can be preferably used glycol type solvents such as ethylene glycol, diethylene glycol and polyethylene glycol, as well as ether type solvents such as diethyl ether and the like so far as they permit the fatty acid-modified ultrafine metal particles to be dispersed without being aggregated or precipitated. Particularly preferably, there can be used ethylene glycol, diethylene glycol, polyethylene glycol and diethyl ether.

(Low-boiling Solvents)

In the dispersion solution containing the fatty acid-modified ultrafine metal particles, the low-boiling solvent used as a dispersion medium for containing fatty acid-modified ultrafine metal particles is a solvent that has a boiling point lower than a boiling point of the high-boiling solvent and that can be isolated from the high-boiling solvent to form two phases. It is important that a difference is small between an SP value of the low-boiling solvent and an SP value of the fatty acid or the glyceride coordinated on the surfaces of the ultrafine metal particles. This makes it possible to extract the fatty acid-modified ultrafine metal particles from the high-boiling solvent and to remove the high-boiling solvent together with the by-products and residues.

It is desired that the low-boiling solvent has a boiling point in a range of, preferably, 40 to 120° C. from the standpoint of productivity and handling of the resin composition layer that constitutes the transparent material.

As the low-boiling solvent, though not limited thereto only, there can be exemplified ketones such as methylbutyl ketone, methyl ethyl ketone, etc.

Among the low-boiling solvents according to the invention, furthermore, it is desired to select a low-boiling solvent that is highly compatible with the fatty acid or the glyceride so that the fatty acid-modified ultrafine metal particles can be efficiently extracted from the high-boiling solvent at the time of isolating the solvents into two phases. Namely, it is desired to so select the low-boiling solvent that a difference (absolute value) is not more than 3 between an SP value (solubility parameter) of the fatty acid or the glyceride coordinated on the surfaces of the particles and an SP value of the low-boiling solvent.

Concretely speaking, if a silver stearate is used as the fatty acid metal salt, there can be preferably used a methylbutyl ketone.

The dispersion solution comprising a solvent in which the fatty acid-modified ultrafine metal particles are dispersed without being aggregated or precipitated, is obtained by mixing the fatty acid-modified ultrafine metal particles and the solvent together, and mixing and dispersing them by using a stirring/dispersing machine having propeller blades, turbine blades or paddle blades, by using a mill-type dispersing machine such as ball mill, beads mill or colloidal mill, or by using a homogenizer, an ultrasonic homogenizer or a high-pressure homogenizer.

In the dispersion solution, the amount of the fatty acid-modified ultrafine metal particles is in a range of, preferably, 0.05 to 5 parts by weight and, specifically, 0.1 to 3 parts by weight per 100 parts by weight of the solvent. If the content of the fatty acid-modified ultrafine metal particles is smaller than the above range, it becomes necessary to add the dispersion solution in large amounts to the curable resin to obtain the antibacterial power as desired causing, however, the formability to be deteriorated. If the content of the fatty acid-modified ultrafine metal particles is larger than the above range, on the other hand, the fatty acid-modified ultrafine metal particles become poorly dispersible.

The dispersion solution has a transmission factor of not less than 80%. Even if added to the photocurable acrylic resins, therefore, the dispersion solution is capable of effectively preventing their excellent transparency from being deteriorated.

EXAMPLES

Measuring the Total Light Ray Transmission Factors

Films having a coating were measured for their total light ray transmission factors by using an SM color computer SM-4S-2 (manufactured by Suga Shikenki Co.).

(Antibacterial Testing)

The antibacterial test was conducted in compliance with the JIS-Z-2801. *Staphylococcus aureus* was used as the bacterial strain. A logarithmic value of a number was regarded to be the antibacterially active value, the number being obtained by dividing the number of bacteria on the untreated film after cultivated by the number of bacteria on the antibacterially treated film after cultivated. The antibacterially active values of not smaller than 2.0 were evaluated to be ◯, and the antibacterially active values of smaller than 2.0 were evaluated to be X.

(Measuring SP Values)

The SP value is synonymous to the solubility parameter, and serves as a rough indication of mixing property between the liquids. If the cohesive energy is denoted by E and the molar volume by V, then the SP value δ is given by $\delta=(E/V)^{1/2}$.

Example 1

3.85 Grams of a silver stearate (SP value of stearic acid: 9.1) and 0.385 g of a saccharin were added to 700 g of a glycerin (SP value: 20), and the mixture thereof was heated at 150° C. for 40 minutes. After the glycerin was cooled down to 60° C., 700 g of a methylisobutyl ketone (SP value: 8.7) was added thereto and stirred. After left to stand still for about one hour, a layer of the methylisobutyl ketone was picked up and a dispersion solution A containing 0.05% by weight of the fatty acid-modified ultrafine silver particles was obtained. From the GC measurement, it was learned that the dispersion solution contained the monostearic acid glyceride (SP value: 10.8) in an amount of 755 ppm.

A photocurable acrylic resin (manufactured by Taisei Fine Chemical Co.) that has been mixed with a diluent in advance, the dispersion solution A containing the fatty acid-modified ultrafine silver particles and a photopolymerization initiator (manufactured by Chiba Specialty Chemical Co.) were mixed into the acrylic resin at such a weight ratio that the amount of the fatty acid-modified ultrafine silver particles was 0.01% by weight to thereby obtain a curable resin composition thereof. By using a bar coater, the curable resin composition was applied onto an easy-to-adhere PET film having a thickness of 100 μm, and was cured by using a UV irradiation apparatus to form a coating of the resin composition in a thickness of 5 μm on the PET film. The obtained film was measured for its transmission factor and was tested for its antibacterial power. The results were as shown in Table 1.

Example 2

A 5 μm-thick coating was formed on the PET film in the same manner as in Example 1 but mixing the photocurable acrylic resin (manufactured by Taisei Fine Chemical Co.) that has been mixed with the diluent in advance, the dispersion solution A containing the fatty acid-modified ultrafine silver particles and the photopolymerization initiator (manufactured by Chiba Specialty Chemical Co.) into the resin at such a weight ratio that the amount of the fatty acid-modified ultrafine silver particles was 0.02% by weight. Optical properties and antibacterial effect of the film were confirmed in the same manner as in Example 1. The results were as shown in Table 1.

Example 3

A 5 μm-thick coating was formed on the PET film in the same manner as in Example 1 but by, further, adding the saccharin in an amount of 0.05% by weight to the dispersion solution A containing the fatty acid-modified ultrafine silver particles. Optical properties and antibacterial effect of the film were confirmed in the same manner as in Example 1. The results were as shown in Table 1.

Comparative Example 1

The photocurable acrylic resin (manufactured by Taisei Fine Chemical Co.) that has been mixed with the diluent in advance and the photopolymerization initiator (manufactured by Chiba Specialty Chemical Co.) were mixed together. By using the bar coater, the mixture thereof was applied onto the easy-to-adhere PET film having a thickness of 100 μm, and was cured by using the UV irradiation apparatus to form a coating of the resin composition thereof in a thickness of 5 μm on the PET film. Optical properties and antibacterial effect of the film were confirmed in the same manner as in Example 1. The results were as shown in Table 1.

Comparative Example 2

0.35 Grams of a powder of silver ion-exchange zeolite was added to 700 g of the methylisobutyl ketone (SP value: 8.7) to obtain a dispersion solution containing 0.05% by weight of the silver ion-exchange zeolite.

The photocurable acrylic resin (manufactured by Taisei Fine Chemical Co.) that has been mixed with the diluent in advance, the dispersion solution containing the silver ion-exchange zeolite and the photopolymerization initiator (manufactured by Chiba Specialty Chemical Co.) were mixed into the resin at such a weight ratio that the amount of the silver ion-exchange zeolite was 0.01% by weight. By using the bar coater, the mixture thereof was applied onto the easy-to-adhere PET film having a thickness of 100 μm, and was cured by using the UV irradiation apparatus to form a coating of the resin composition thereof in a thickness of 5 μm on the PET film. Optical properties and antibacterial effect of the film were confirmed in the same manner as in Example 1. The results were as shown in Table 1.

Comparative Example 3

7 Grams of the powder of silver ion-exchange zeolite was added to 700 g of the methylisobutyl ketone (SP value: 8.7) to obtain a dispersion solution containing 1% by weight of the silver ion-exchange zeolite.

The photocurable acrylic resin (manufactured by Taisei Fine Chemical Co.) that has been mixed with the diluent in advance, the dispersion solution containing the silver ion-exchange zeolite and the photopolymerization initiator (manufactured by Chiba Specialty Chemical Co.) were mixed into the resin at such a weight ratio that the amount of the silver ion-exchange zeolite was 0.5% by weight. By using the bar coater, the mixture thereof was applied onto the easy-to-adhere PET film having a thickness of 100 μm, and was cured by using the UV irradiation apparatus to form a coating of the resin composition thereof in a thickness of 5 μm on the PET film. Optical properties and antibacterial effect of the film were confirmed in the same manner as in Example 1. The results were as shown in Table 1.

Comparative Example 4

To 700 g of the methylisobutyl ketone (SP value: 8.7), there was added 0.35 g of a powder of the fatty acid-modified ultrafine silver particles that has been obtained in advance by heating the silver stearate in a nitrogen atmosphere at 270° C. followed by refining, and the mixture thereof was stirred and mixed to obtain a dispersion solution B containing 0.05% by weight of the ultrafine silver particles modified with the fatty acid. The GC measurement indicated the presence of no monostearic acid glyceride in the dispersion solution. The photocurable acrylic resin (manufactured by Taisei Fine Chemical Co.) that has been mixed with the diluent in advance, the dispersion solution B containing the ultrafine silver particles modified with the fatty acid and the photopolymerization initiator (manufactured by Chiba Specialty Chemical Co.) were mixed into the resin at such a weight ratio that the amount of the ultrafine silver particles modified with the fatty acid was 0.01% by weight. By using the bar coater, the mixture thereof was applied onto the easy-to-adhere PET film having a thickness of 100 μm, and was cured by using the UV irradiation apparatus to form a coating of the resin composition thereof in a thickness of 5 μm on the PET film. Optical properties and antibacterial effect of the film were confirmed in the same manner as in Example 1. The results were as shown in Table 1.

Comparative Example 5

The photocurable acrylic resin (manufactured by Taisei Fine Chemical Co.) that has been mixed with the diluent in advance, the powder of the fatty acid-modified ultrafine silver particles that has been obtained in advance by heating the silver stearate in a nitrogen atmosphere at 270° C. followed by refining and the photopolymerization initiator (manufactured by Chiba Specialty Chemical Co.) were mixed into the resin at such a weight ratio that the amount of the ultrafine silver particles modified with the fatty acid was 0.01% by weight. By using the bar coater, the mixture thereof was applied onto the easy-to-adhere PET film having a thickness of 100 μm, and was cured by using the UV irradiation apparatus to form a coating of the resin composition thereof in a thickness of 5 μm on the PET film. The obtained film contained aggregates that could be confirmed with the eye. The coating was, therefore, judged to be defective.

TABLE 1

| | Dispersion solution to be mixed to UV acrylic resin | Content of particles in coating (wt %) | Total light transmission factor (%) | Antibacterially active value | | Remarks |
|---|---|---|---|---|---|---|
| Ex. 1 | Fatty acid-modified ultrafine silver particle-containing dispersion solution A | 0.01 | 93 | ◯ | ≥4.9 | |
| Ex. 2 | Fatty acid-modified ultrafine silver particle-containing dispersion solution A | 0.02 | 92.8 | ◯ | ≥4.9 | |
| Ex. 3 | Fatty acid-modified ultrafine silver particle-containing dispersion solution A | 0.01 | 93 | ◯ | ≥4.9 | * |
| Comp. Ex. 1 | none | 0 | 93 | X | 0.1 | |
| Comp. Ex. 2 | Dispersion solution containing silver ion-exchange zeolite | 0.01 | 92 | X | 0.1 | |
| Comp. Ex. 3 | Dispersion solution containing silver ion-exchange zeolite | 0.5 | 79 | ◯ | 3.5 | |
| Comp. Ex. 4 | Fatty acid-modified ultrafine silver particle-containing dispersion solution B | 0.01 | 90 | X | 1.5 | |

*: 0.05 wt % of saccharin was added to the dispersion solution

INDUSTRIAL APPLICABILITY

The curable resin composition of the present invention contains the fatty acid-modified ultrafine metal particles that are dispersed therein without being aggregated and, therefore, exhibits excellent antibacterial power as well as excellent transparency. Upon being used as a material for coating a variety of kinds of products, therefore, the curable resin composition of the invention imparts antibacterial power to the products.

Further, the coating comprising the curable resin composition of the invention features excellent transparency as well as excellent scratch resistance, anti-fouling property and anti-glaring property and, therefore, is useful as a hard coating formed on the films for protecting liquid crystal display devices. Namely, the coating comprising the curable resin composition of the invention is capable of imparting antibacterial power to the films for protecting liquid crystal display devices. The resin composition can, further, be used for forming a top coating of the printed matters and the packaging materials.

The invention claimed is:

1. A curable resin composition including a curable resin, an ion stabilizer and ultrafine metal particles dispersed in the curable resin, wherein the ultrafine metal particles are modified with a fatty acid, the fatty acid is coordinated on surfaces of the ultrafine metal particles, and a glyceride is coordinated around said fatty acid or on the surfaces of the ultrafine metal particles, said curable resin being a photo-curable acrylic resin.

2. The curable resin composition according to claim 1, wherein said ultrafine metal particles are the ultrafine silver particles.

3. The curable resin composition according to claim 1, wherein the curable resin composition contains a dispersion solution that contains the ultrafine metal particles modified with the fatty acid; and
the dispersion solution that contains the ultrafine metal particles modified with the fatty acid is a low-boiling solvent that contains the ultrafine metal particles modified with the fatty acid, that is obtained by using a glycerin as a high-boiling solvent, adding a fatty acid metal salt of a metal of any one of Ag, Cu or Zn and a saccharin to said high-boiling solvent, heating and mixing them together to thereby prepare the high-boiling solvent in which the ultrafine metal particles modified with the fatty acid are dispersed, the ultrafine metal particles modified with the fatty acid being the ultrafine metal particles of any one of Ag, Cu or Zn and having the fatty acid and the glyceride coordinated on the surfaces thereof, mixing said high-boiling solvent in which the ultrafine metal particles modified with the fatty acid are dispersed and a low-boiling solvent together and, thereafter, isolating said high-boiling solvent and the low-boiling solvent into two phases so that the ultrafine metal particles modified with the fatty acid are extracted from said high-boiling solvent into said low-boiling solvent.

4. The curable resin composition according to claim 3, wherein the low-boiling solvent is methylisobutyl ketone or methyl ethyl ketone.

5. The curable resin composition according to claim 3, wherein a difference is not more than 3 between a solubility parameter (SP value) of the fatty acid or the glyceride and a solubility parameter (SP value) of the low-boiling solvent.

6. The curable resin composition according to claim 1, wherein the ultrafine metal particles are fatty acid-modified ultrafine metal particles having an average primary particle diameter of not more than 100 nm.

* * * * *